United States Patent
Hagihara et al.

(10) Patent No.: US 10,470,644 B2
(45) Date of Patent: Nov. 12, 2019

(54) OPTICAL CONNECTOR AND MEDICAL EQUIPMENT

(71) Applicants: SONY OLYMPUS MEDICAL SOLUTIONS INC., Hachioji-shi (JP); SONY CORPORATION, Tokyo (JP)

(72) Inventors: Masahiro Hagihara, Tokyo (JP); Kei Tomatsu, Kanagawa (JP); Kenji Sakamoto, Aichi (JP)

(73) Assignees: SONY CORPORATION, Tokyo (JP); SONY OLYMPUS MEDICAL SOLUTIONS INC., Tokyo (JP)

( * ) Notice: Subject to any disclaimer, the term of this patent is extended or adjusted under 35 U.S.C. 154(b) by 426 days.

(21) Appl. No.: 15/308,225

(22) PCT Filed: May 15, 2015

(86) PCT No.: PCT/JP2015/064034
§ 371 (c)(1),
(2) Date: Nov. 1, 2016

(87) PCT Pub. No.: WO2015/198743
PCT Pub. Date: Dec. 30, 2015

(65) Prior Publication Data
US 2017/0049301 A1    Feb. 23, 2017

(30) Foreign Application Priority Data

Jun. 27, 2014  (JP) .................................. 2014-133331

(51) Int. Cl.
*A61B 1/00*    (2006.01)
*A61B 1/04*    (2006.01)
(Continued)

(52) U.S. Cl.
CPC ...... *A61B 1/00126* (2013.01); *A61B 1/00006* (2013.01); *A61B 1/00009* (2013.01);
(Continued)

(58) Field of Classification Search
CPC ............ A61B 1/00126; A61B 1/00006; A61B 1/00117; A61B 1/00009; A61B 1/07;
(Continued)

(56) References Cited

U.S. PATENT DOCUMENTS 5,239,983 A  *  8/1993  Katsurada .......... A61B 1/00124
                                                       439/171
5,894,369 A  *  4/1999  Akiba ................ A61B 1/00096
                                                       348/65
(Continued)

FOREIGN PATENT DOCUMENTS

JP   4-122353 A   4/1992
JP   5-176884 A   7/1993
(Continued)

OTHER PUBLICATIONS

International Search Report dated Aug. 11, 2015 in PCT/JP2015/064034 filed May 15, 2015.
(Continued)

*Primary Examiner* — Timothy J Neal
(74) *Attorney, Agent, or Firm* — Xsensus LLP (57) ABSTRACT

A plug as an optical connector is configured to connect mechanically and optically with a receptacle, wherein part of an optical fiber for transmitting an optical signal is disposed internally. The plug includes a tubular plug-side first outer wall into which the optical fiber is inserted, configured to cover an optical signal-emitting end of the optical fiber. An end side of the plug-side first outer wall to be connected to the receptacle is sealed by a plug-side cover member translucent to an optical signal. In the optical connector intrusion of liquid and foreign substances can be suppressed, and reliability of optical communication can be ensured.

17 Claims, 4 Drawing Sheets

(51) Int. Cl.
*A61B 1/06* (2006.01)
*A61B 1/07* (2006.01)
*G02B 23/24* (2006.01)

(52) U.S. Cl.
CPC ...... *A61B 1/00114* (2013.01); *A61B 1/00117* (2013.01); *A61B 1/00124* (2013.01); *A61B 1/00128* (2013.01); *A61B 1/042* (2013.01); *A61B 1/0669* (2013.01); *A61B 1/07* (2013.01); *G02B 23/2476* (2013.01)

(58) Field of Classification Search
CPC . A61B 1/00124; A61B 1/00128; A61B 1/042; A61B 1/0669; A61B 1/00114; G02B 23/2476
See application file for complete search history.

(56) References Cited

U.S. PATENT DOCUMENTS

| | | | |
|---|---|---|---|
| 6,030,339 | A | 2/2000 | Tatsuno et al. |
| 6,053,923 | A * | 4/2000 | Veca ................ A61B 17/32002 606/79 |
| 6,099,465 | A * | 8/2000 | Inoue ...................... A61B 1/05 348/75 |
| 8,488,969 | B1 * | 7/2013 | Masarik ................ H04B 10/22 398/113 |
| 2005/0254751 | A1 | 11/2005 | Ushiro et al. |
| 2008/0281157 | A1 * | 11/2008 | Miyagi .............. A61B 1/00126 600/132 |
| 2009/0264706 | A1 * | 10/2009 | Bala .................. A61B 1/00096 600/160 |
| 2011/0184244 | A1 * | 7/2011 | Kagaya .............. A61B 1/00117 600/182 |
| 2014/0016942 | A1 | 1/2014 | Masarik |
| 2014/0050485 | A1 | 2/2014 | Masarik et al. |
| 2015/0155941 | A1 | 6/2015 | Masarik et al. |
| 2015/0229395 | A1 | 8/2015 | Masarik |
| 2015/0288448 | A1 | 10/2015 | Masarik |
| 2016/0173743 | A1 | 6/2016 | Masarik |
| 2017/0078022 | A1 | 3/2017 | Masarik et al. |

FOREIGN PATENT DOCUMENTS

| | | |
|---|---|---|
| JP | 2001-296446 A | 10/2001 |
| JP | 2004-325522 A | 11/2004 |
| JP | 2006-146077 A | 6/2006 |
| JP | 2008-278971 A | 11/2008 |
| JP | 2009-56240 A | 3/2009 |
| JP | 2013-101312 A | 5/2013 |

OTHER PUBLICATIONS

Office Action dated Apr. 3, 2018 in corresponding Japanese Patent Application No. 2014-133331, 5 pages.
Extended European Search Report dated Jan. 12, 2018 in Patent Application No. 15811067.6.
Combined Chinese Office Action and Search Report dated Oct. 25, 2017 in Patent Application No. 201580033400.5 (with English language translation).
Office Action dated Sep. 11, 2018 in corresponding European Patent Application No. 15 811 067.6, 4 pages.
Office Action dated Oct. 16, 2018 in corresponding Japanese Patent Application No. 2014-133331, 6 pages.

* cited by examiner

OPTICAL CONNECTOR AND MEDICAL EQUIPMENT

TECHNICAL FIELD

The present disclosure relates to an optical connector and medical equipment.

BACKGROUND ART

There has been conventionally known an optical connector, such as a plug and a receptacle, to be mechanically and optically connected with a mating connector (for example, see Patent Literature 1).

In such an optical connector, a portion of an optical fiber for transmitting an optical signal is usually disposed in a tubular outer wall. Furthermore, the same applies to the mating connector. The optical connector is to be mechanically connected to the mating connector by the outer wall. This connection allows an optical signal-receiving end of one optical fiber and an optical signal-emitting end of the other optical fiber, or an optical signal-emitting end of one optical fiber and an optical signal-receiving end of the other optical fiber, to face each other, thereby enabling transmission (optical communication) between the optical fibers.

CITATION LIST

Patent Literature

Patent Literature 1: JP H5-176884A

SUMMARY

Technical Problem

By the way, when liquid such as water or a foreign substance intrudes into the optical connector, there is a risk that the liquid or the foreign substance impairs reliabilty of optical communication.

Especially, the optical connector described in Patent Literature 1 is used in an endoscope apparatus for inspecting a test subject. Such an endoscope apparatus is subjected to a sterilization treatment by a so-called autoclave and a disinfection treatment with a disinfection solution, prior to the inspection of a test subject. Accordingly, moisture or liquid such as a disinfection liquid is likely to intrude into the optical connector.

Therefore there is a desire for a technology that enables intrusion by liquid and foreign substances to be suppressed, and reliability of optical communication to be ensured.

The present disclosure has been achieved in view of the above description, and has an object to provide an optical connector and medical equipment, in which intrusion of liquid and foreign substances can be suppressed, and reliability of optical communication can be ensured.

Means for Solving the Problem

In order to solve the above problem and achieve the object, according to the present disclosure, an optical connector configured to connect mechanically and optically with a mating connector, wherein part of an optical transmission line thereof configured to transmit an optical signal is disposed internally, includes a tubular first outer wall into which the optical transmission line is inserted, configured to cover an optical signal-receiving end or an optical signal-emitting end of the optical transmission line. An end side of the first outer wall to be connected to the mating connector is sealed by a cover member translucent to an optical signal.

In the optical connector according to the present disclosure, in the above invention, a collimator lens may be disposed between the optical signal-receiving end or the optical signal-emitting end and the cover member.

In the optical connector according to the present disclosure, in the above invention, an end surface of the cover member facing to the optical signal-receiving end or the optical signal-emitting end may be flat, and an anti-reflective coating film may be disposed on the end surface.

In the optical connector according to the present disclosure, in the above invention, art end surface of the cover member facing to the optical signal-receiving end or the optical signal-emitting end may be flat, and may be tilted with respect to an imaginary plane orthogonal to a central axis of the optical transmission line.

In the optical connector according to the present disclosure, in the above invention, the cover member may include a plate body having a first plate surface serving as the end surface, and a second plate surface parallel to the first plate surface.

In the optical connector according to the present disclosure, in the above invention, the end surface of the cover member may be tilted at an angle of 1 degree or more and 45 degrees or less with respect to the imaginary plane.

In the optical connector according to the present disclosure, in the above invention, the cover member may be disposed in a position which is shifted from an end of the first outer wall toward an inside of the first outer wall.

In the optical connector according to the present disclosure, in the above invention, the cover member may be joined to the first outer wall by soldering, brazing, bonding, or glass sealing.

In the optical connector according to the present disclosure, in the above invention, a circumference of the optical transmission line in the first outer wall may be sealed by sealing material.

In the optical connector according to the present disclosure, in the above invention, the cover member may include a single crystal of sapphire.

The optical connector according to the present disclosure may, in the above invention, further include: a tubular second outer wall to which the first outer wall is engaged and through which the optical transmission line is inserted; a printed circuit board disposed in the second outer wall; and an electrical contact point configured to electrically connect with the mating connector and to electrically connect the mating connector and the printed circuit board. Circumferences of the optical transmission line and the printed circuit board in the second outer wall may be sealed by sealing material.

According to the present disclosure, medical equipment configured to image a test subject includes the optical connector.

The medical equipment according to the present disclosure may, in the above invention, further include: an endoscope configured to image an inside of a test subject and to output an optical signal based on an imaging signal; and a control apparatus configured to input the optical signal via a first transmission cable and a second transmission cable and to control operation of the endoscope. The first transmission cable and the second transmission cable may be configured to connect to each other by the optical connector and a mating connector configured to mechanically and electrically connect to the optical connector.

In the medical equipment according to the present disclosure, in the above invention, the optical connector may be attached to the first transmission cable to be connected to the endoscope, out of the first transmission cable and the second transmission cable.

Advantageous Effects of Invention

In the optical connector according to the present disclosure, an end side of the first outer wall to be connected to a mating connector is sealed by a cover member having translucency.

In other words, since the cover member has translucency, optical communication through the cover member is enabled. Furthermore, sealing of the end of the first outer wall by the cover member enables intrusion of liquid and foreign substances into the first outer wall to be suppressed, and reliability of optical communication to be ensured.

The medical equipment according to the present disclosure includes the above-described optical connector, and therefore exerts effects similar to those of the above-described optical connector.

DESCRIPTION OF EMBODIMENTS

Hereinafter, a mode for carrying out the present disclosure (hereinafter, referred to as an "embodiment") will be described with reference to the drawings. Furthermore, the present disclosure is not limited by an embodiment described below. Furthermore, in the description of the drawings, the same reference numeral is assigned to the same portion.

[Schematic Configuration of Endoscope Apparatus]

Figure 1:
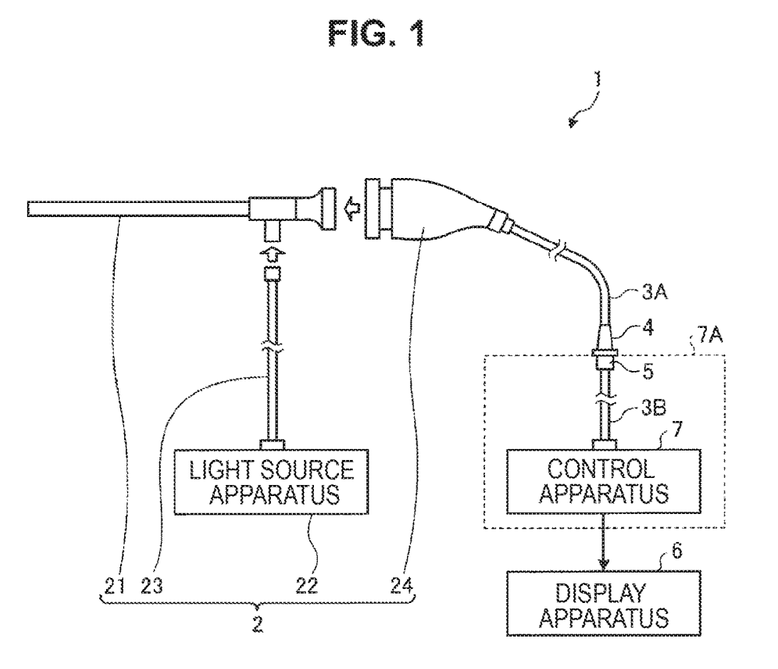
FIG. 1 is a view illustrating a schematic configuration of an endoscope apparatus according to the present disclosure.

FIG. 1 is a view illustrating a schematic configuration of an endoscope apparatus 1 according to an embodiment of the present disclosure.

The endoscope apparatus 1 is an apparatus used in the medical field and used for observing an inside of an observation object such as a human body (an inside of a living body). In other words, the endoscope apparatus 1 is equivalent to the medical equipment according to the present disclosure. This endoscope apparatus 1 includes, as illustrated in FIG. 1, an endoscope 2, first and second transmission cables 3A and 3B, a plug 4, a receptacle 5, a display apparatus 6, and a control apparatus 7.

Furthermore, although an endoscope apparatus including a rigid endoscope (an insertion section 21 (FIG. 1)) in the endoscope 2 will be described as the endoscope apparatus 1 in the present embodiment, the endoscope apparatus is not limited to this configuration, and may include a flexible endoscope (not shown) in the endoscope 2. Furthermore, although an endoscope having a camera head 24 (FIG. 1) and including the camera head 24 and the insertion section 21 in a separated manner will be described as the endoscope 2, the endoscope is not limited to this configuration, and may include the insertion section 21 and the camera head 24 in a unified manner, Also, the endoscope 2 may be an endoscope apparatus constituted by a probe for ultrasonic tests (an ultrasonic endoscope).

The endoscope 2 images an inside of a living body (inside of a test subject) and outputs an imaging signal thereof. This endoscope 2 includes, as illustrated in FIG. 1, the insertion section 21, a light source apparatus 22, a light guide 23, and the camera head 24.

The insertion section 21 is hard and slender, and is to be inserted into a living body. Inside this insertion section 21, there is provided an optical system which is constituted by one or more lenses and is to concentrate light to form a subject image.

The light source apparatus 22 is connected to one end of the light guide 23 and is to supply the one end of the light guide 23 with light for illuminating an inside of a living body.

One end of the light guide 23 is removably connected to the light source apparatus 22, and the other end thereof is to be removably connected to the insertion section 21. The light guide 23 transmits light supplied by the light source apparatus 22 from the one end to the other end to supply the insertion section 21 with the light. The light supplied to the insertion section 21 is emitted from the end of the insertion section 21 to illuminate an inside of a living body. The light (subject image) radiated into a living body is concentrated by the optical system inside the insertion section, 21.

The camera head 24 is to be removably connected to a base end of the insertion section 21. This camera head 24 includes: an imaging element (not shown) for imaging a subject image and outputting an imaging signal (electrical signal); and a photoelectric conversion element (not shown) for converting the imaging signal (electrical signal) output from the imaging element into an optical signal. The camera head 24 images the subject image formed by light concentration in the insertion section 21, converts an imaging signal (electrical signal) by the imaging into an optical signal, and outputs the converted optical signal, under control by the control apparatus 7.

Figure 4:
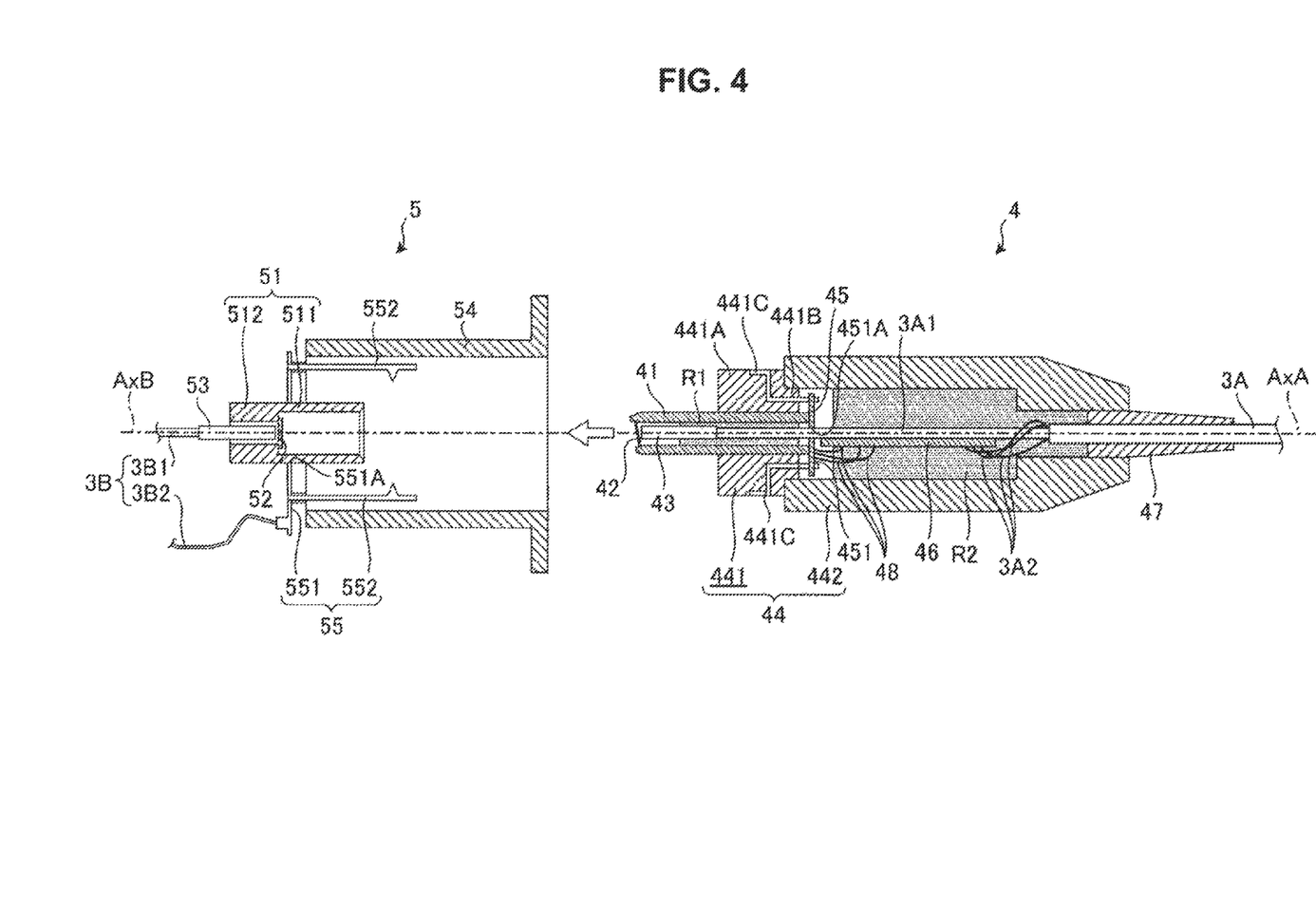
FIG. 4 is a cross-sectional view of a cut plane running along a central axis of the plug and the receptacle illustrated in FIG. 2.

A first transmission cable 3A is a composite cable including, inside an outer sheath (not shown) as the outermost layer, an optical fiber 3A1 (see FIG. 4) that is an optical transmission line for transmitting an optical signal (imaging signal) output from the camera head 24; and a plurality of electrical signal cables 3A2 (see FIG. 4). One end of the first transmission cable 3A is connected to the camera head 24.

A second transmission cable 3B is, similarly to the first transmission cable 3A, a composite cable including an optical fiber 3B1 (see FIG. 2 and FIG. 4) and a plurality of electrical signal cables 3B2 (see FIG. 4). One end of the second transmission cable 3B is connected to the control apparatus 7.

The plug 4 is a male connector, and corresponds to the optical connector according to the present disclosure. The plug 4 is attached to the other end of the first transmission cable 3A.

The receptacle 5 is a female connector. The receptacle 5 is attached to the other end of the second transmission cable 3B.

The above-described plug 4 and receptacle 5 are connected to each other, thereby enabling the electrical and optical connection and the transmission of an electrical signal and an optical signal between the first and second transmission cables 3A and 3B.

Here, if the receptacle 5 is disposed to a casing 7A (shown by the dashed line in FIG. 1) of the control apparatus 7, the receptacle 5 is fixed to the casing 7A of the control apparatus 7, thereby facilitating attachment and removal between the plug 4 and the receptacle 5. However, the disposition of the receptacle 5 to the casing 7A of the control apparatus 7 is not essential, and the receptacle 5 may be alternatively disposed outside the casing 7A.

Details for configurations of the plug 4 and the receptacle 5 will be described later.

The display apparatus 6 displays an image under control of the control apparatus 7.

The control apparatus 7 is constituted by a Central Processing, Unit (CPU), a Graphics Processing Unit (GPU), or the like, and centrally controls operation of the camera head 24 and the display apparatus 6.

Specifically, the control apparatus 7 acquires an optical signal (imaging signal) output from the camera head 24 through the first and second transmission cables 3A and 3B (optical fibers), and converts the optical signal into an electrical signal. Then, the control apparatus 7 performs various image processing, to the converted electrical signal, thereby enabling the image imaged by the camera head 24 to be displayed on the display apparatus 6. Furthermore, the control apparatus 7 outputs a control signal and the like to the camera head 24 through the first and second transmission cables 3A and 3B (electrical signal cables).

[Configurations of Plug and Receptacle]

Figure 2:
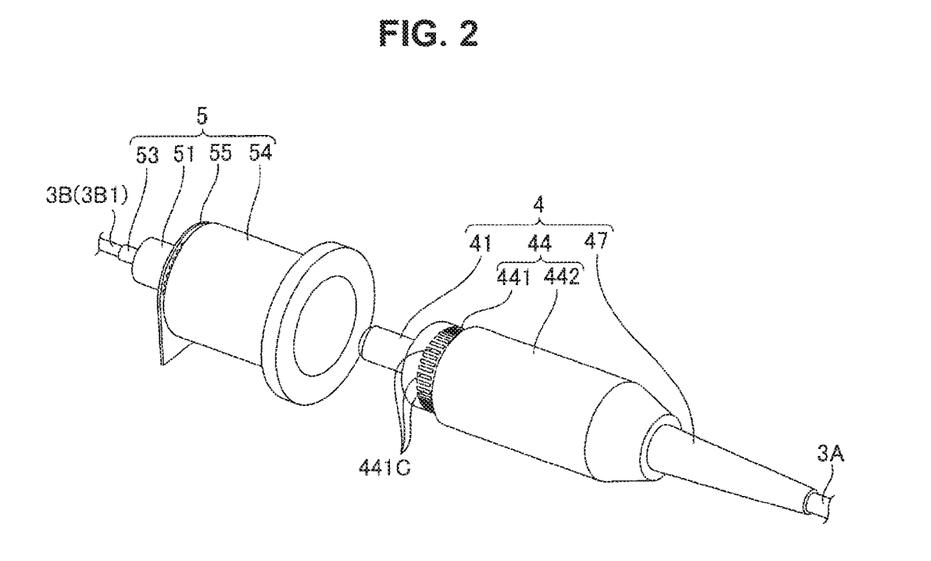
FIG. 2 is an exploded perspective view of the plug and the receptacle illustrated in FIG. 1 seen from a base end side of the plug.
Figure 3:
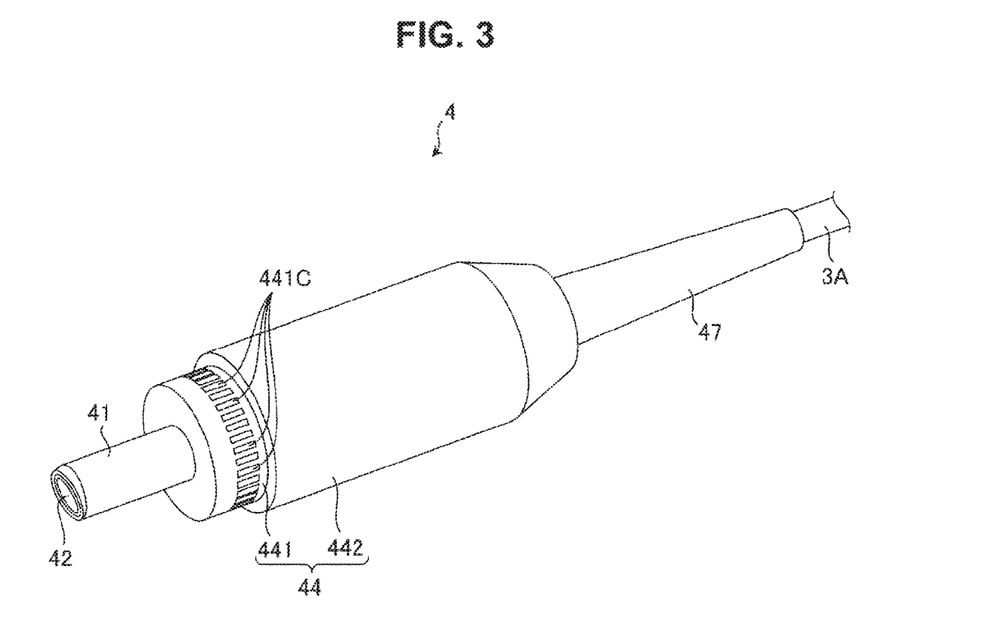
FIG. 3 is a perspective view of the plug illustrated in FIG. 2 seen from an end side.

Next, configurations of the plug 4 and the receptacle 5 will be described,

FIG. 2 is an exploded perspective view of the plug 4 and the receptacle 5 seen from a base end side (camera head 24 side) of the plug 4. FIG. 3 is a perspective view of the plug 4 seen from the end side (the side to which the receptacle 5 is connected). FIG. 4 is a cross-sectional view of a cut plane running along the central axis of the plug 4 and the receptacle 5.

Hereinafter, the configuration of the plug 4 and the configuration of the receptacle 5 will be described in this order.

[Configuration of Plug]

The plug 4 includes, as illustrated in FIG. 2 to FIG. 4, a plug-side first outer wall 41, a plug-side cover member 42 (FIG. 3 and FIG. 4), a plug-side collimator 43 (FIG. 4), a plug-side second outer wall 44, a connector section 45 (FIG. 4), a plug-side printed circuit board 46 (FIG. 4), and an elastic member 47.

The plug-side first outer wall 41 is a member corresponding to the first outer wall according to the present disclosure, and has a substantially cylindrical shape as illustrated in FIG. 2 to FIG. 4. Furthermore, the shape of the plug-side first outer wall 41 is not limited to a cylindrical shape as long as it is tubular. The plug-side first outer wall 41 may be configured as a tubular body having a cross-sectional shape of an ellipse, rectangle, square, polygon, or the like. The optical fiber 3A1 constituting the first transmission cable 3A is inserted into the plug-side first outer wall 41 along the central axis of the plug-side first outer wall 41. Thus, the plug-side first outer wall 41 covers an optical signal-emitting end of the optical fiber 3A1.

Figure 5:
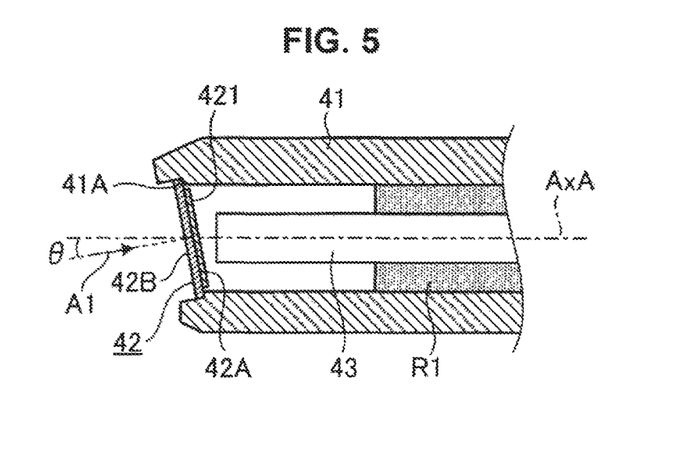
FIG. 5 is an enlarged view of the end portion of the plug-side first outer wall illustrated in FIG 4.

FIG. 5 is an enlarged view of the end portion of the plug-side first outer wall 41 illustrated in FIG. 4.

The inner circumferential edge of this plug-side first outer wall 41 is provided with an attachment section 41A for attaching the plug-side cover member 42 as illustrated in FIG. 5.

Specifically, the attachment section 41A is, as illustrated in FIG. 5, a recess which sinks in a direction A1 which is tilted at angle θ with respect to a central axis (optical axis) AxA of the optical fiber 3A1 inserted into the plug 4. The bottom of this attachment section 41A is formed to be flat. The normal direction of the bottom comes to be a direction tilted at angle θ with respect to the central axis AxA.

The plug-side cover member 42 is a member corresponding to the cover member according to the present disclosure. Such a plug-side cover member 42 is formed in the substantially same planar shape as the attachment section 41A seen from the direction A1, and is constituted by a plate body having first and second plate surfaces 42A and 42B (FIG. 5) which are parallel to each other. The plug-side cover member 42 is applied against the bottom of the attachment section 41A, and is air-tightly joined to the plug-side first outer wall 41 (the attachment section 41A) by soldering, brazing, bonding, or glass sealing.

Such joining allows the first plate surface 42A to face the optical signal-emitting end of the optical fiber 3A1 and to be fronted by the inside of the plug-side first outer wall 41. Furthermore, the plug-side cover member 42 comes to take a posture in which the first and second plate surfaces 42A and 42B are tilted at angle θ with respect to an imaginary plane orthogonal to the central axis AxA (a posture in which the normal line of the first and second plate surfaces 42A and 42B is tilted at angle θ with respect to the central axis AxA). Furthermore, the plug-side cover member 42 is disposed in a position that is shifted from the end of the plug-side first outer wall 41 toward the inside of the plug-side first outer wall 41 (a position secluded from the end).

Here, the above-described angle θ is preferably 1 degree or more and 45 degrees or less, and more preferably equal to or greater than 5 degrees and equal to or less than 20 degrees, When angle θ is 1 degree or more, there is provided an effect of reducing the light reflected toward the plug-side collimator 43. When angle θ is greater than 45 degrees, the area of the plug-side cover member 42 needs to be increased in order to perform optical transmission. Accordingly, there are needed not only increased size of the plug-side cover member 42 but also higher processing accuracy and assembling accuracy than when the tilt is smaller. For this reason, angle θ is preferably 45 degrees or less. Angle θ for sulking the best balance among the light reflected toward the plug-side collimator 43, the size of a window member, the processing accuracy, and the assembling accuracy is 5 degrees or more and 20 degrees or less, and this angle range is the most preferable.

Although the plug-side cover member 42 includes a single crystal of sapphire having tolerance to heat and chemicals in the present embodiment, the plug-side cover member 42 is not limited to this configuration, and may include other materials such as glass as long, as the material is a member translucent to an optical signal. The cover member, either on the plug 4 side (the plug-side cover member 42) or on the receptacle 5 side (a receptacle-side Cover member 52 (FIG. 4)), is required to have a transmittance allowing optical communication to be established. Furthermore, disposition of an anti-reflective coating film reduces reflection on the surface of the cover member, enabling efficient light transmission. The plug-side cover member 42 is preferably provided with an anti-reflective coating film on both faces. When the anti-reflective coating film is provided, angle θ does not necessarily need to have a tilt. Although being effective even at 0 degrees, it is more effective when angle θ is the above-described angle.

The plug 4 is disposed to the first transmission cable 3A connected to the camera head 24. For this reason, when the anti-reflective coating film is disposed on an outer surface (the second plate surface 42B) of the plug 4, the anti-reflective coating film has a risk of deteriorating from autoclave treatment. Chemical solution treatment and the like. Therefore, the anti-reflective coating film is preferably disposed to at least an inner surface (the first plate surface 42A) of the plug 4, because the inside of the plug 4 is sealed thereby to be unlikely to be affected by temperature and chemicals, and the anti-reflective coating film effectively functions.

Consequently, in the present embodiment, an anti-reflective coating film 421 is disposed to the first plate surface 42A of the plug-side cover member 42, as illustrated in FIG. 5.

The plug-side collimator 43 is a member corresponding to the collimator lens according to the present disclosure, and is joined to the optical signal-emitting end of the optical fiber 3A1 inside the plug-side first outer wall 41, as illustrated in FIG. 4. In other words, the plug-side collimator 43 is disposed between the plug-side cover member 42 and the optical signal-emitting end of the optical fiber 3A1. The plug-side collimator 43 transforms light (optical signal) emitted from the optical signal-emitting end of the optical fiber 3A1 into parallel light.

Inside the above-described plug-side first outer wall 41, the base end side of the plug-side first outer wall 41 (a circumference of a portion of the plug-side collimator 43 and a circumference of the optical signal-emitting end side of the optical fiber 3A1) is sealed by an adhesive sealing material R1 such as silicone resin and epoxy resin, as illustrated in FIG. 4 or FIG. 5. Furthermore, the material used for the sealing is not limited to the above-described sealing material R1 such as resin, and may be other materials such as glass.

The plug-side second outer wall 44 is a member corresponding to the second outer wall according to the present disclosure. The plug-side second outer wall 44 includes, as illustrated in FIG. 2 to FIG. 4, an end-side outer wall 441 and a base end-side outer wall 442, and has an entirely substantially cylindrical Shape. Furthermore, the shape of the plug-side second outer wall 44 is not limited to a cylindrical shape as long as it is tubular, and may be configured as a tubular body having a cross-sectional shape of an ellipse, rectangle, square, or polygon.

As illustrated in FIG. 2 to FIG. 4, the end-side outer wall 441 has an entirely substantially cylindrical shape, and includes: a cylindrical large outer diameter section 441A; and a cylindrical small outer diameter section 441B having an outer diameter dimension smaller than the outer diameter dimension of the large outer diameter section 441A and having the same inner diameter dimension as the inner diameter dimension of the large outer diameter section 441A. Both sections 441A and 441B are integrally formed on an identical axis. The base end portion of the plug-side first outer wall 41 is engaged to the end-side outer wall 441 such that the end portion of the plug-side first outer wall 41 projects.

Here, the boundary between the end-side outer wall 441 and the plug-side first outer wall 41 is sealed by an adhesive sealing material such as O-ring, silicone resin, and epoxy resin.

This end-side outer wall 441 is provided with, as illustrated in FIG. 2 to FIG. 4, a plurality of plug-side electrical contact points 441C including a conductive material.

As illustrated in FIG. 4, one end of each of the plug-side electrical contact points 441C is exposed an outer circumferential surface of the large outer diameter section 441A, and extends from the outer circumferential surface to the end surface of the base end side of the small outer diameter section 441B so that the other end projects from the end surface of the base end side. The plurality of plug-side electrical contact points 441C is disposed at a predetermined distance along the circumferential direction of the end-side outer wall 441.

As illustrated in FIG. 2 to FIG. 4, the base end-side outer wall 442 is disposed on the base end side to the end-side outer wall 441, and has a substantially cylindrical shape. The end portion of the base end-side outer wall 442 is engaged to the small outer diameter section 441B in a state where the first transmission cable 3A is inserted into the base end-side outer wall 442.

Here, the boundary between the base end-side outer wall 442 and the small outer diameter section 441B is sealed by an adhesive sealing material such as O-ring, silicone resin, and epoxy resin.

As illustrated in FIG. 4, the connector section 45 is disposed inside the base end-side outer wall 442, and relays (electrically connects) the plurality of plug-side electrical contact points 441C and the plug-side printed circuit board 46. This connector section 45 includes: a flat plate-like insulator 451 having a hole 451A into which the optical fiber 3A1 is inserted; and a plurality of contacts (not shown) which includes a conductive material and penetrates both sides of the insulator 451. The connector section 45 is disposed inside the base end-side outer wall 442 in a posture where the insulator 451 is orthogonal to the central axis AxA. Each of the plurality of contacts is electrically connected to each of the plurality of plug-side electrical contact points 441C projecting from the end surface of the base end side of the small outer diameter section 441B, and is electrically connected to the plug-side printed circuit board 46 through electrical wires 48.

As illustrated in FIG. 4, the plug-side printed circuit board 46 is disposed along the plane having the central axis AxA, and relays, via the connector section 45, the plurality of plug-side electrical contact points 441C and the plurality of electrical signal cables 3A2 constituting the first transmission cable 3A.

Inside the above-described base end-side outer wall 442, the base end side of the base end-side outer wall 442 (a circumference of a portion of the first transmission cable 3A and a circumference of the plug-side printed circuit board 46) is sealed by a sealing material R2 such as silicone resin and epoxy resin, as illustrated in FIG. 4. Furthermore, the material used for the sealing is not limited to the above-described sealing material R2 such as resin, and may be other materials such as glass.

The elastic member 47 is a member for inhibiting the first transmission cable 3A from bending around the inner circumferential edge of the base end portion of the base end-side outer wall 442, and has a substantially cylindrical shape including elastic material, such as rubber. The end portion of the elastic member 47 is engaged to the base end portion of the base end-side outer wall 442 in a state where the first transmission cable 3A is inserted into the elastic member 47.

Here, the boundary between the elastic member 47 and the base end-side outer wall 442 is sealed by an adhesive sealing material such as O-ring, silicone resin, and epoxy resin.

[Configuration of Receptacle]

The receptacle 5 includes, as illustrated in FIG. 2 or FIG. 4, a receptacle-side first outer wall 51, a receptacle-side cover member 52 (FIG. 4), a receptacle-side collimator 53, a receptacle-side second outer wall 54, and a receptacle-side printed circuit board 55.

As illustrated in FIG. 2 or FIG. 4, the receptacle-side first outer wall 51 has an entirely substantially cylindrical shape, and includes: a cylindrical large inner diameter section 511 located on the end side (the side to be connected to the plug 4); and a cylindrical small inner diameter section 512 being located on the base end side and having an inner diameter dimension smaller than the inner diameter dimension of the large inner diameter section 511 and the same outer diameter dimension as the outer diameter dimension of the large inner diameter section 511. Both the sections 511 and 512 are integrally formed on an identical axis. Furthermore, the shape of the receptacle-side first outer wall 51 is not limited to a cylindrical shape as long as it is tubular, and may be configured as a tubular body having a cross-sectional shape of an ellipse, rectangle, square, polygon, or the like.

The inner diameter size of the large inner diameter section 511 is somewhat larger than the outer diameter dimension of the plug-side first outer wall 41. Also, the length dimension (the dimension in the height direction of the cylinder) of the large inner diameter section 511 is somewhat larger than the dimension of the projection, which is a portion of the plug-side first outer wall 41, from the plug-side second outer wall 44 (the end-side outer wall 441).

The receptacle-side cover member 52 is constituted by a plate body having translucency. The receptacle-side cover member 52 is applied against a stepped portion between the large inner diameter section 511 and the small inner diameter section 512, and is joined to the receptacle-side first outer wall 51. In other words, the receptacle-side cover member 52 is disposed in a posture of being orthogonal to a central axis (optical axis) AxB of the optical fiber 3B1 (FIG. 4), unlike the above-described plug-side cover member 42. A method of such joining may be the same as the method of joining the plug-side cover member 42 to the plug-side first outer wall 41, or may be other methods. A material of the receptacle-side cover member 52 may be the same as the material of the plug-side cover member 42, or may be other materials.

The receptacle-side collimator 53 is inserted into the small inner diameter section 512 in a state where it is joined to an optical signal-receiving end of the optical fiber 3B1, as illustrated in FIG. 4. The receptacle-side collimator 53 leads light (optical signal) emitted from the plug-side collimator 43 to the optical signal-receiving end of the optical fiber 3B1.

The receptacle-side second outer wall 54 has an entirely substantially cylindrical shape, and has an inner diameter sin that is somewhat lamer than the outer diameter dimension of the plug-side second outer wall 44 (the base end-side outer wall 442), as illustrated in FIG. 2 or FIG. 4. The end portion of the receptacle-side first outer wall 51 is inserted into the receptacle-side second outer wall 54 such that the base end portion of the receptacle-side first outer wall 51 projects.

The receptacle-side printed circuit board 55 includes, as illustrated in FIG. 2 or FIG. 4, a base plate body 551 and a plurality of receptacle-side electrical contact points 552.

The base plate body 551 has, as illustrated in FIG. 4, a hole 551A penetrating both sides of a substantially central portion of the base plate body 551. Furthermore, the receptacle-side first outer wall 51 is engaged in the hole 551A.

The plurality of receptacle-side electrical contact points 552 is constituted by conductive material, and is electrically connected to the base plate body 551, Also, the receptacle-side electrical contact points 552 project toward the inside of the receptacle-side second outer wall 54. These receptacle-side electrical contact points 552 are disposed at a predetermined distance along the circumferential direction of the receptacle-side first outer wall 51. The number of receptacle-side electrical contact points 552 to be disposed is the same as the number of plug-side electrical contact points 441C.

Furthermore, the base plate body 551 relays the plurality of receptacle-side electrical contact points 552 and the plurality of electrical signal cables 3B2 (FIG. 4) constituting the second transmission cable 3B.

In the state where the plug 4 and the receptacle 5 are mechanically connected to each other, the plug-side first outer wall 41 is inserted into the receptacle-side first outer wall 51 the large inner diameter section 511). In this state, the central axis AxA of the optical fiber 3A1 and the central axis AxB of the optical fiber 3131 coincide with each other, and the plug-side collimator 43 (the optical signal-emitting end of the optical fiber 3A1) and the receptacle-side collimator 53 (the optical signal-receiving end of the optical fiber 3B1) face each other. In other words, in this state (a state where optical communication is enabled), an optical signal (imaging signal) output from the camera head 24 onto the first transmission cable 3A (the optical fiber 3A1) can be transmitted to the second transmission cable 3B (the control apparatus 7) through the plug 4 and the receptacle 5.

In such a state where the plug 4 and the receptacle 5 are mechanically connected to each other, the plug-side second outer wall 44 is inserted into the receptacle-side second outer wall 54, and the plurality of plug-side electrical contact points 441C and the plurality of receptacle-side electrical contact points 552 are electrically connected to each other in a corresponding manner. Furthermore, in this state, a control signal or the like output from the control apparatus 7 onto the second transmission cable 3B (the plurality of electrical signal cables 3B2) can be transmitted to the first transmission cable 3A (the camera head 24) through the plug 4 and the receptacle 5.

In the plug 4 according to the present embodiment as described above, the end of the plug-side first outer wall 41 is sealed by the plug-side cover member 42 having translucency.

In other words, since the plug-side cover member 42 has translucency, optical communication through the plug-side cover member 42 is enabled. Furthermore, sealing of the end of the plug-Side first miter wall 41 by the plug-side cover member 42 enables intrusion of liquid and foreign substances into the plug-side first outer wall 41 to be suppressed, and reliability of optical communication to be ensured.

In addition, in the plug 4 according to the present embodiment, the plug-side collimator 43 is disposed between the optical signal-emitting end of the optical fiber 3A1 and the plug-side cover member 42. Similarly, the receptacle-side collimator 53 is disposed in the receptacle 5 according to the present embodiment.

For this reason, the accuracy of the mechanical connection between the plug 4 and the receptacle 5 is not required to be as high as that in the configuration in which the plug-side collimator 43 and the receptacle-side collimator 53 are omitted. Consequently the plug 4 and the receptacle 5 can be easily manufactured.

By the way, the insertion section 21, the light guide 23, the camera head 24, and the first transmission cable 3A are members which require a sterilization treatment by a so-called autoclave and a disinfection treatment with a disinfection solution or the like.

The plug 4 according to the present embodiment is attached to the first transmission cable 3A, of the first and second transmission cables 3A and 3B. The first transmission cable 3A is connected to the camera head 24. The plug-side cover member 42 includes a single crystal of sapphire having tolerance to heat and chemicals. Furthermore, the plug-side cover member 42 is air-tightly joined to the plug-side first outer wall 41 by soldering, brazing, bonding, or glass sealing. Also, the inside of the plug-side first outer wall 41 and the inside of the plug-side second outer wall 44 (the inside of the base end-side outer wall 442) are sealed by the sealing materials R1 and R2.

For this reason, even when the above-described sterilization treatment and disinfection treatment are performed, intrusion of moisture and liquid such as a disinfection liquid into the plug-side first outer wall 41 can be sufficiently suppressed by attaching the plug 4 to the first transmission cable 3A.

By the way, when the plug-side cover member 42 includes sapphire glass having high reflectance, a portion of the light emitted from the plug-side collimator 43 can be reflected at the plug-side cover member 42, and become stray light, compromising the reliability of the optical communication.

On the contrary, in the plug 4 according to the present embodiment, the plug-side cover member 42 is disposed in a posture where the first and second plate surfaces 42A and 42B are tilted at angle θ with respect to an imaginary plane orthogonal to the central axis AxA.

For this reason, even when a portion of the light emitted from the plug-side collimator 43 is reflected at the plug-side cover member 42, the reflected tight comes to proceed in a direction that avoids the plug-side collimator 43. Therefore, the reflected light does not become stray light, enabling reliability of optical communication to be sufficiently ensured.

Furthermore, in the plug 4 according to the present embodiment, the plug-side cover member 42 is disposed in a position that is shifted from the end of the plug-side first outer wall 41 toward the inside of the plug-side first outer wall 41 (a secluded position in the plug-side first outer wall 41).

Accordingly, the plug-side cover member 42 is unlikely to be touched by hand, thereby suppressing adhesion of foreign substances to the plug-side cover member 42. In other words, foreign substances do not compromise the reliability of the optical communication.

(Other Embodiments)

Although an embodiment for carrying out the present disclosure has been described, the present disclosure should not be limited to the above-described embodiment.

Figure 6:
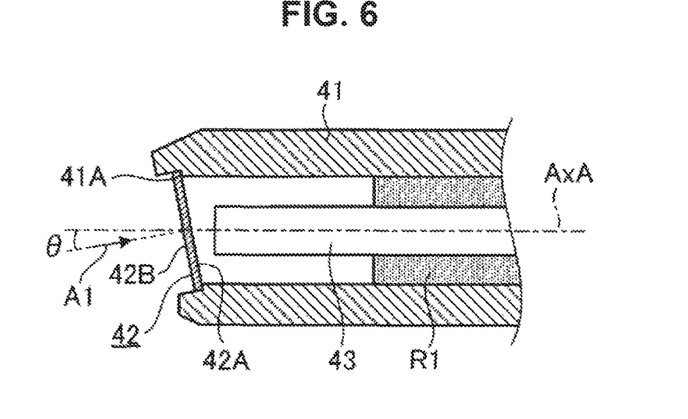
FIG. 6 is a view illustrating a variation of an embodiment according to the present disclosure.

FIG. 6 is a view illustrating a at of an embodiment according to the present disclosure. Specifically, FIG. 6 is a view corresponding to FIG. 5, and is an enlarged view of the end portion of the plug-side first outer wall 41.

Although the anti-reflective coating film 421 is disposed on the plug-side cover member 42 in the above-described embodiment, the present disclosure is not limited to this configuration, and may not include the anti-reflective coating film 421 as illustrated in FIG. 6. Even when such a configuration is employed, effects similar to those in the above-described embodiment can be exerted.

Figure 7:
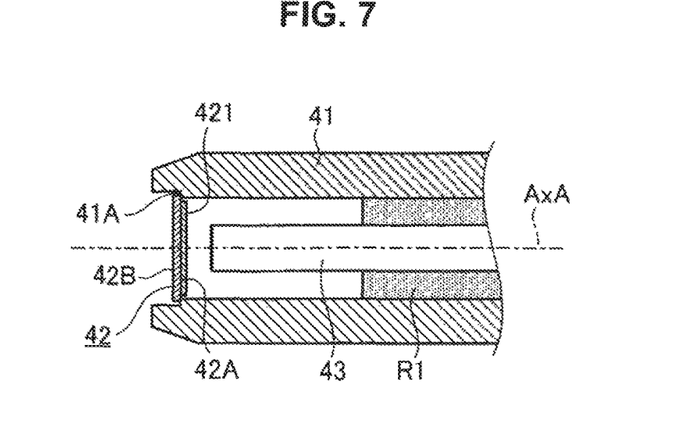
FIG. 7 is a view illustrating a variation of an embodiment according to the present disclosure.

FIG. 7 is a view illustrating a variation of an embodiment according to the present disclosure. Specifically. FIG. 7 is a view corresponding to FIG. 5, and is an enlarged view of the end portion of the plug-side first outer wall 41.

Although the plug-side cover member 42 is tilted and joined at angle θ to the plug-side first outer wall 41 in the above described embodiment, the present disclosure is not limited to this configuration, and may be configured such that angle θ is 0 degrees as illustrated in FIG. 7. Even when such a configuration is employed, effects similar to those in the above-described embodiment can be exerted.

In the above-described embodiment, the plug 4 as a male connector is the optical connector according to the present disclosure, and the receptacle 5 as a female connector is the mating connector. However, the present disclosure is not limited to this configuration, and may be configured to include a receptacle as the optical connector according to the present disclosure and a plug as the mating connector.

Although the first plate surface 42A of the plug-side cover member 42 is flat in the above-described embodiment, the present disclosure is not limited to this configuration, and may be configured such that it is curved. Even when the first plate surface is curved in this manner, the present disclosure is preferably configured such that the light emitted from the plug-side collimator 43 and reflected on the first plate surface proceeds in the direction that avoids the plug-side collimator 43.

Although optical communication is performed through one channel (communication path) in the above-described embodiment, the present disclosure is not limited to this configuration, and may include a plurality of channels. When optical communication is performed through a plurality of channels in this manner, a cover member may be provided for each channel, or the plurality of channels may be bundled into one or more groups such that the number of cover members to be disposed is smaller than the number of channels.

In the above-described embodiment, the optical connector according to the present disclosure is used in the endoscope apparatus 1. However, the present disclosure is not limited to this configuration, and the optical connector according to the present disclosure may be used in other medical equipment for transmitting optical signals or in industrial fields, and in other electronic equipment such as an endoscope apparatus for observing an inside of an observation object such as machines and structures.

Additionally, the present technology may also be configured as below.

(1)

An optical connector configured to connect mechanically and optically with a mating connector, wherein part of an optical transmission line thereof configured to transmit an optical signal is disposed internally, the optical connector including a tubular first outer wall into which the optical transmission line is inserted, configured to cover an optical signal-receiving end or an optical signal-emitting end of the optical transmission line, wherein an end side of the first outer wall to be connected to the mating connector is sealed by a cover member translucent to an optical signal.

(2)

The optical connector according to (1), wherein a collimator lens is disposed between the optical signal-receiving end or the optical signal-emitting end and the cover member.

(3)

The optical connector according to (1) or (2), wherein an end surface of the cover member facing to the optical signal-receiving end or the optical signal-emitting end is flat, and an anti-reflective coating film is disposed on the end surface.

(4)

The optical connector according to any one of (1) to (3), wherein an end surface of the cover member facing to the optical signal-receiving end or the optical signal-emitting end is flat, and is tilted with respect to an imaginary plane orthogonal to a central axis of the optical transmission line.

(5)

The optical connector according to (4), wherein the cover member includes a plate body having a first plate surface serving as the end surface, and a second plate surface parallel to the first plate surface.

(6)

The optical connector according to (4) or (5), wherein the end surface of the cover member is tilted at an angle of 1 degree or more and 45 degrees or less with respect to the imaginary plane.

(7)

The optical connector according to any one of (1) to (6), wherein the cover member is disposed in a position which is shifted from an end of the first outer wall toward an inside of the first outer wall.

(8)

The optical connector according to any one of (1) to (7), wherein the cover member is joined to the first outer wall by soldering, brazing bonding, or glass sealing.

(9)

The optical connector according to any one of (1) to (8), wherein a circumference of the optical transmission line in the first outer wall is sealed by sealing material.

(10)

The optical connector according to any one of (1) to (9), wherein the cover member includes a single crystal of sapphire.

(11)

The optical connector according to any one of (1) to (10), further including:

a tubular second outer wall to which the first outer wall is engaged and through which the optical transmission line is inserted;

a printed circuit board disposed In the second outer wall; and an electrical contact point configured to electrically connect with the mating connector and to electrically connect the mating connector and the printed circuit board, wherein circumferences of the optical transmission line and the printed circuit board in the second outer wall are sealed by sealing material.

(12)

Medical equipment configured to image a test subject, the medical equipment including the optical connector according to any one of (1) to (11).

(13)

The medical equipment according to (12), further including:

an endoscope configured to image an inside of a test subject and to output an optical signal based on an imaging signal; and a control apparatus configured to input the optical signal via a first transmission cable and a second transmission cable and to control operation of the endoscope, wherein the first transmission cable and the second transmission cable are configured to connect to each other by the optical connector and a mating connector configured to mechanically and electrically connect to the optical connector.

(14)

The medical equipment according to (13), wherein the optical connector is attached to the first transmission cable to be connected to the endoscope, out of the first transmission cable and the second transmission cable.

REFERENCE SYMBOLS LIST 1 endoscope apparatus
2 endoscope
3A first transmission cable
3A1 optical fiber
3A2 electrical signal cable
3B second transmission cable
3B1 optical fiber
3B2 electrical signal cable
4 plug
5 receptacle
6 display apparatus
7 control apparatus
21 insertion section
22 light source apparatus
23 light guide
24 camera head
41 plug-side first outer wall
41A attachment section
42 plug-side cover member
42A first plate surface
42B second plate surface
43 plug-side collimator
44 plug-side second outer wall
45 connector section
46 plug-side printed circuit board
47 elastic member
48 electrical wires
51 receptacle-side first outer wall
52 receptacle-side cover member
53 receptacle-side collimator
54 receptacle-side second outer wall
55 receptacle-side printed circuit board
421 anti-reflective coating film
441 end-side outer wall
441A large outer diameter section
441B small outer diameter section
441C plug-side electrical contact point
442 base end-side outer wall
451 insulator
451A hole
511 large inner diameter section
512 small inner diameter section
551 base plate body
551A hole 552 receptacle-side electrical contact point
A1 direction
AxA, AxB central axis
R1, R2 sealing material
θ angle

The invention claimed is:

1. An optical connector for an endoscopic device comprising:
   an optical transmission line configured to transmit an optical signal corresponding to image data obtained by the endoscopic device;
   an outer wall, into which the optical transmission line is inserted, having an end portion via which optical communication is accomplished with a mating connector; and
   a translucent cover material, which airtightly seals the outer wall proximate to the end portion, wherein
   the translucent cover material is arranged on an optical path of the optical communication, and
   an inside surface of the translucent cover material is flat and is tilted with respect to an imaginary plane orthogonal to a central axis of the optical transmission line.

2. The optical connector according to claim 1, wherein a collimator lens is disposed within the outer wall and on the optical path of the optical communication downstream, when optical signal-receiving, or upstream, when optical signal-emitting, of the translucent cover material.

3. The optical connector according to claim 1, wherein an anti-reflective coating film is disposed on the inside surface.

4. The optical connector according to claim 1, wherein the translucent cover material includes a plate body including:
   a first plate surface serving as the inside surface, and
   a second plate surface parallel to the first plate surface.

5. The optical connector according to claim 1, wherein the inside surface of the translucent cover material is tilted at an angle of 1 degree or more and 45 degrees or less with respect to the imaginary plane.

6. The optical connector according to claim 1, wherein the translucent cover material is disposed in a position which is shifted from the end portion of the outer wall toward an inside of the outer wall.

7. The optical connector according to claim 1, wherein the translucent cover material is joined to the first outer wall by soldering, brazing, bonding, or glass sealing.

8. The optical connector according to claim 1, wherein a circumference of the optical transmission line in the outer wall is sealed by sealing material.

9. The optical connector according to claim 1, wherein the translucent cover material comprises a single crystal of sapphire.

10. The optical connector according to claim 1, further comprising:
    a larger outer wall to which the outer wall is engaged and through which the optical transmission line is inserted;
    a printed circuit board disposed in the larger outer wall; and
    one or more electrical contact points configured to electrically connect with the mating connector and to electrically connect the mating connector and the printed circuit board,
    wherein circumferences of the optical transmission line and the printed circuit board in the larger outer wall are sealed by sealing material.

11. The optical connector according to claim 10, wherein the one or more electrical contact points are arranged on a round connecting portion of the larger outer wall.

12. The optical connector according to claim 10, wherein the one or more electrical contact points and the optical transmission line are nearly coaxially arranged.

13. The optical connector according to claim 10, wherein the outer wall and the larger outer wall are each tubular shaped walls.

14. A medical equipment for imaging a subject, the medical equipment comprising:
    an optical connector configured to connect mechanically and optically with a mating connector, wherein
       part of an optical transmission line configured to transmit an optical signal resulting from the imaging is disposed internally to the optical connector, and
       the optical connector includes an outer wall, into which the optical transmission line is inserted, having an end portion via which optical communication is accomplished with the mating, connector; and
    a translucent cover material, which airtightly seals the outer wall proximate to the end portion, wherein
    the translucent cover material is arranged on an optical path of the optical communication, and
    an inside surface of the translucent cover material is flat and is tilted with respect to an imaginary plane orthogonal to a central axis of the optical transmission line.

15. The medical equipment according to claim 14, further comprising:
    an endoscope configured to image an inside of a subject and to output an optical signal based on an imaging signal; and
    control circuitry configured to input the optical signal via a first transmission cable and a second transmission cable and to control operation of the endoscope,
    wherein the first transmission cable and the second transmission cable are configured to connect to each other by the optical connector and the mating connector each being configured to mechanically and electrically connect to each other.

16. The medical equipment according to claim 15, wherein the optical connector is attached to the first transmission cable connected to the endoscope.

17. An endoscope system comprising:
    a camera configured to generate an image signal;
    camera control circuitry configured to process the image signal, the camera control circuitry having an optical connector plug receptacle; and
    a camera cable, connected to the camera, configured to transmit the image signal as an optical signal, the camera cable having an optical connector plug that includes:
       an optical transmission line configured to transmit the optical signal,
       an outer wall, into which the optical transmission line is inserted, having an end portion via which optical communication is accomplished with a mating connector, and
       a translucent cover material, which airtightly seals the outer wall proximate to the end portion, wherein
    the translucent cover material is arranged on an optical path of the optical communication, and
    an inside surface of the translucent cover material is flat and is tilted with respect to an imaginary plane orthogonal to a central axis of the optical transmission line.

* * * * *